US011260128B2

(12) United States Patent
Vo-Dinh et al.

(10) Patent No.: US 11,260,128 B2
(45) Date of Patent: Mar. 1, 2022

(54) SYNERGISTIC NANOTHERAPY SYSTEMS AND METHODS OF USE THEREOF

(71) Applicant: Duke University, Durham, NC (US)

(72) Inventors: Tuan Vo-Dinh, Chapel Hill, NC (US); Brant A. Inman, Durham, NC (US); Paolo Maccarini, Durham, NC (US); Greg Palmer, Durham, NC (US); Yang Liu, Durham, NC (US); Douglas Weitzel, Durham, NC (US)

(73) Assignee: Duke University, Durham, NC (US)

( * ) Notice: Subject to any disclaimer, the term of this patent is extended or adjusted under 35 U.S.C. 154(b) by 747 days.

(21) Appl. No.: 15/852,598

(22) Filed: Dec. 22, 2017

(65) Prior Publication Data

US 2018/0133319 A1 May 17, 2018

Related U.S. Application Data

(63) Continuation of application No. PCT/US2016/038729, filed on Jun. 22, 2016.
(Continued)

(51) Int. Cl.
| | | |
|---|---|---|
| *A61K 41/00* | (2020.01) | |
| *A61N 5/00* | (2006.01) | |
| *A61N 5/06* | (2006.01) | |
| *B22F 1/00* | (2006.01) | |
| *C07K 16/28* | (2006.01) | |
| *A61K 33/242* | (2019.01) | |
| *A61K 47/69* | (2017.01) | |
| *A61P 35/02* | (2006.01) | |
| *A61P 35/04* | (2006.01) | |
| *A61P 35/00* | (2006.01) | |
| *A61B 18/14* | (2006.01) | |
| *A61B 18/18* | (2006.01) | |
| *A61B 18/20* | (2006.01) | |
| *A61K 9/00* | (2006.01) | |

(Continued)

(52) U.S. Cl.
CPC .......... *A61K 41/0052* (2013.01); *A61B 18/14* (2013.01); *A61B 18/1815* (2013.01); *A61B 18/20* (2013.01); *A61K 9/0019* (2013.01); *A61K 9/0053* (2013.01); *A61K 9/51* (2013.01); *A61K 33/24* (2013.01); *A61K 33/242* (2019.01); *A61K 39/39558* (2013.01); *A61K 47/6929* (2017.08); *A61N 1/403* (2013.01); *A61N 5/00* (2013.01); *A61N 5/025* (2013.01); *A61N 5/062* (2013.01); *A61N 5/0625* (2013.01); *A61P 35/00* (2018.01); *A61P 35/02* (2018.01); *A61P 35/04* (2018.01); *B22F 1/0022* (2013.01); *C07K 16/2827* (2013.01); *A61B 2018/00577* (2013.01); *A61B 2018/1807* (2013.01); *A61K 2039/505* (2013.01); *A61K 2039/54* (2013.01); *A61K 2039/545* (2013.01); *A61K 2039/55555* (2013.01); *A61K 2039/572* (2013.01); *A61N 5/067* (2021.08); *A61N 2005/0659* (2013.01); *A61N 2005/0661* (2013.01); *A61N 2005/0662* (2013.01); *B22F 2999/00* (2013.01)

(58) Field of Classification Search
CPC .......... A61K 41/0052; A61K 2039/505; A61K 2039/54; A61K 2039/545; A61K 2039/572; A61K 9/0019; A61K 9/0053; A61K 9/51; A61K 33/24; A61K 39/39558; A61K 2039/55555; A61K 33/242; A61K 47/6929; A61P 35/02; A61P 35/04; A61P 35/00; A61B 18/14; A61B 18/1815; A61B 18/20; A61B 2018/00577; A61B 2018/1807; B22F 2999/00; B22F 1/0022; A61N 2005/0659; A61N 2005/0661; A61N 2005/0662; A61N 1/403; A61N 5/025; A61N 5/0625; A61N 5/067; A61N 5/00; A61N 5/062; C07K 16/2827

See application file for complete search history.

(56) References Cited

U.S. PATENT DOCUMENTS

| | | | |
|---|---|---|---|
| 2011/0021970 A1* | 1/2011 | Vo-Dinh | A61K 41/0042 604/20 |
| 2013/0261444 A1 | 10/2013 | Green et al. | |

(Continued)

OTHER PUBLICATIONS

Liu et al. Synergistic Immuno Photothermal Nanotherapy (SYM-PHONY) for the Treatment of Unresectable and Metastatic Cancers. Scientific Reports 7: 1-6, published online Aug. 17, 2017.*

(Continued)

*Primary Examiner* — Alana Harris Dent
(74) *Attorney, Agent, or Firm* — NK Patent Law

(57) ABSTRACT

The presently disclosed subject matter is directed to a method of treating cancer, such as (but not limited to) metastatic bladder and breast cancer. The disclosed method comprises using two treatment modalities to synergistically treat primary and secondary tumor cells in a subject. The first element of the method comprises administering a therapeutically effective amount of a plasmonics-active metal nanoparticle to a subject comprising a primary cancer and a distant metastatic site, wherein the nanoparticle concentrates at the primary cancer. The method further comprises exposing the subject to photon radiation at the site of the primary cancer. The second element of the disclosed method comprises administering a therapeutically effective amount of an immune checkpoint modulator to the subject. The synergistic combination provides a rapid, safe, and effective treatment of local and distant lesions, better than each modality alone.

5 Claims, 9 Drawing Sheets

Related U.S. Application Data

(60) Provisional application No. 62/182,734, filed on Jun. 22, 2015.

(51) Int. Cl.

| | |
|---|---|
| A61K 9/51 | (2006.01) |
| A61K 33/24 | (2019.01) |
| A61K 39/395 | (2006.01) |
| A61N 1/40 | (2006.01) |
| A61N 5/02 | (2006.01) |
| A61K 39/00 | (2006.01) |
| A61N 5/067 | (2006.01) |
| A61B 18/00 | (2006.01) |

(56) References Cited

U.S. PATENT DOCUMENTS

2014/0065135 A1  3/2014  Irving et al.
2015/0037818 A1  2/2015  Huang et al.

OTHER PUBLICATIONS

Liu et al. (Theranostics 5(9): 946-960 and supplementary materials: 6 pages, published May 23, 2015.*
Ahmed, K. et al.: "Hyperthermia: an effective strategy to induce apoptosis in cancer cells.", Apoptosis (2015) 20: 1411-1419.
Albrecht, M. G. et al.: "Anomalously Intense Raman Spectra of Pyridine at a Silver Electrode", J. Am. Chem. Soc., 99:15, Jul. 20, 1977, 5215-5217.
Boncheva, M. et al.: "Design of Oligonucleotide Arrays at Interfaces", Langmuir 1999, 15, 4317-4320.
Burges, J. D. et al.: "Octadecyl Mercaptan Sub-monolayers on Silver Electrodeposited on Gold Quartz Crystal Microbalance Electrodes", Langmuir 1997, 13, 3781-3786.
Wang, C. et al.: "Immunological Responses Triggered by Photothermal Therapy with Carbon Nanotubes in Combination with Anti-CTLA-4 Therapy to Inhibit Cancer Metastasis", Advanced Materials 2014, vol. 26, Issue 48.
Chen, D. S. et al.: "Molecular Pathways: Next-Generation Immunotherapy—Inhibiting Programmed Death-Ligand 1 and Programmed Death-1", Clin Cancer Res., 18(24), Dec. 15, 2012, 6580-6587.
Chen, D. S. et al.: "Oncology Meets Immunology: The Cancer-Immunity Cycle", Immunity 39, Jul. 25, 2013, 1-10.
Cheng, W. et al.: "Synthesis and Self-Assembly of Cetyltrimethylammonium Bromide-Capped Gold Nanoparticles", Langmuir 2003, 19, 9434-9439.
Chowdhury, F. et al.: "PD-L1 and CD8(+)PD1(+) lymphocytes exist as targets in the pediatric tumor microenvironment for immunomodulatory therapy", OncoImmunology 4(10), Oct. 2015.
Eifler, A. C. et al.: "Nanoparticle Therapeutics: FDA Approval, Clinical Trials, Regulatory Pathways, and Case Study", Biomedical Nanoetechnology: Methods and Protocols, Methods in Molecular Biology, vol. 726: 325-338.
Evans, S. S. et al.: "Fever and the thermal regulation of immunity: the immune system feels the heat", Nature Reviews Immunology 15, Jun. 2015, 335-349.
Ewens, A. et al.: "Distant Metastasis from Subcutaneously Grown E0771 Medullary Breast Adenocarcinoma", Anticancer Research, 2005, vol. 25, 3905-391.
Fales, A. M. et al.: "Silica-coated gold nanostars for combined surface-enhanced Raman scattering (SERS) detection and singletoxygen generation: a potential nanoplatform for theranostics", Langmuir 2011, 27, 12186-12190.
Fleischmann, M. et al.: "Raman Spectra of Pyridine Adsorbed at a Silver Electrode", J. Chem. Phys. Lett., 26 (2), May 15, 1974, 163-166.
Gandra, N. et al.: "Tunable and amplified Raman gold nanoprobes for effective tracking (TARGET): in vivo sensing and imaging", Nanoscale, 2016, 8, 8486-8494.
Gandra, N. et al.: "Inherently Stealth and Highly Tumor-Selective Gold Nanoraspberries for Photothermal Cancer Therapy", Nature Scientific Reports, 5:10311 (2015).
Garg, A. D. et al.: "Immunogenic cell death, DAMPs and anticancer therapeutics: an emerging amalgamation", Biochim Biophys Acta 1805 (2010) 53-71.
Koning, G. A. et al.: "Hyperthermia and Thermosensitive Liposomes for Improved Delivery of Chemotherapeutic Drugs to Solid Tumors", Pharmaceutical Research (2010) 27: 1750-1754.
Herne, T. M. et al.: "Characterization of DNA Probes Immobilized on Gold Surfaces", J. Am. Chem. Soc. 1997, 119, 8916-8920.
Hirsch, L. R. et al.: "Nanoshell-mediated near-infrared thermal therapy of tumors under magnetic resonance guidance", PNAS, Nov. 11, 2003, 100 (23), 13549-13554.
Huang, X. et al.: "Plasmonic photothermal therapy (PPTT) using gold nanoparticles", Lasers Medical Science (2008) 23: 217-228.
Ito, A. et al.: "Tumor regression by combined immunotherapy and hyperthermia using magnetic nanoparticles in an experimental subcutaneous murine melanoma", Cancer Science, Mar. 2003, 94 (3), 308-313.
Jeanmaire, D. L. et al.: "Surface Raman Spectroelectrochemistry. Part I. Heterocyclic, Aromatic, and Aliphatic Amines Adsorbed on the Anodized Silver Electrode", J. Electroanal. Chem., 84 (1977) 1-20.
Keir, M. E. et al.: "PD-1 and its ligands in tolerance and immunity", Annu Rev Immunol. 2008, 26: 677-704.
Khoury, C. G. et al.: "Gold Nanostars For Surface-Enhanced Raman Scattering: Synthesis, Characterization and Optimization", J Phys Chem C 2008, 112 (48), 18849-18859.
Liu, Y. et al.: "Quintuple-modality (SERS-MRI-CT-TPL-PTT) plasmonic nanoprobe for theranostics", Nanoscale, 2013, 5, 12126-12131.
Loo, C. et al.: "Nanoshell-enabled photonics-based imaging and therapy of cancer", Technology in Cancer Research & Treatment, vol. 3, No. 1, Feb. 2004, 33-40.
Maeda, H.: "The enhanced permeability and retention (EPR) effect in tumor vasculature: the key role of tumor-selective macromolecular drug targeting", Adv Enzyme Regul, vol. 41, 189-207, 2001.
Ngo, H. T. et al.: "Sensitive DNA detection and SNP discrimination using ultrabright SERS nanorattles and magnetic beads for malaria diagnostics", Biosensors and Bioelectronics 81 (2016) 8-14.
Steel, A. B. et al.: "Electrochemical Quantitation of DNA Immobilized on Gold", Anal. Chem. 1998, 70, 4670-4677.
Takada, T. et al.: "Growth inhibition of re-challenge B16 melanoma transplant by conjugates of melanogenesis substrate and magnetite nanoparticles as the basis for developing melanoma-targeted chemo-thermo-immunotherapy", J Biomed Biotechnol 2009.
Tanaka, K. et al.: "Heat immunotherapy using magnetic nanoparticles and dendritic cells for T-lymphoma", J Biosci Bioeng, vol. 100, No. 1, 112-115, 2005.
Pandita, T. K. et al.: "Molecular Parameters of Hyperthermia for Radiosensitization", Crit Rev Eukaryot Gene Expr. 2009; 19(3): 235-251.
Toraya-Brown, S. et al.: "Local Hyperthermia Treatment of Tumors Induces CD8+ T Cell-mediated Resistance against Distal and Secondary Tumors", Nanomedicine, Aug. 2014, 10(6): 1273-1285.
Tsan, M.-F. et al.: "Heat shock proteins and immune system", Journal of Leukocyte Biology, vol. 85, Jun. 2009, 905-910.
Vo-Dinh, T.: "Surface-Enhanced Raman Spectroscopy Using Metallic Nanostructures", Trends in Anal. Chem., vol. 17, Nos. 8+9, 1998, 557-582.
Vo-Dinh, T., et al.: "Plasmonics-based nanostructures for surface-enhanced Raman scattering bioanalysis", Methods in Molecular Biology, vol. 300: 255-283, 2005.
Vo-Dinh, T. et al.: "Plasmonic nanoprobes: from chemical sensing to medical diagnostics and therapy", Nanoscale, Nov. 7, 2013, 5(21): 10127-10140.
Xia, X. et al.: "Gold nanocages as multifunctional materials for 30 nanomedicine", Frontiers of Physics, 2014, 9(3): 378-384.
Yuan, H. et al.: "TAT peptide-functionalized gold nanostars: enhanced intracellular delivery and efficient NIR photothermal therapy using ultralow irradiance", Journal of the American Chemical Society. Jul. 18, 2012; 134(28): 11358-11361.

(56) References Cited

OTHER PUBLICATIONS

Yuan, H. et al.: "Gold nanostars: surfactant-free synthesis, 3D modelling, and two-photon photoluminescence imaging", Nanotechnology, Feb. 24, 2012; 23(7): 075102.
Yuan, H. et al.: "In vivo particle tracking and photothermal ablation using plasmon-resonant gold nanostars", Nanomedicine, Nov. 2012, 8(8): 1355-1363.
ISA/US, International Search Report and Written Opinion of PCT Patent Application No. PCT/US2016/038729, dated Sep. 23, 2016.
WIPO, International Preliminary Report on Patentability of PCT Patent Application No. PCT/US2016/038729, dated Dec. 26, 2017.

* cited by examiner

SYNERGISTIC NANOTHERAPY SYSTEMS AND METHODS OF USE THEREOF

CROSS REFERENCE TO RELATED APPLICATIONS

The presently disclosed subject matter is a continuation of PCT Patent Application No. PCT/US2016/038729 filed on Jun. 22, 2016 and entitled "SYNERGISTIC NANOTHERAPY SYSTEMS AND METHODS OF USE THEREOF", which claims the benefit of U.S. Provisional Patent Application Ser. No. 62/182,734 filed Jun. 22, 2015 and entitled "SYNERGISTIC IMMUNO PHOTO NANOTHERAPY SYSTEMS AND METHODS OF USE", the entire disclosure of all of which is incorporated herein by reference.

TECHNICAL FIELD

This presently disclosed subject matter is directed to synergistic nanotherapy systems and to methods of their use.

BACKGROUND

In spite of recent advances in the detection and treatment of cancer, there remains no cure for the disease. In recent years, immunotherapy using specific immune checkpoint modulators has provided a promising way to disrupt the tumor immunosuppressive environment. However, current methods employ antibodies that are effective only for a limited number of patients and can become ineffective over time. It would therefore be beneficial to provide a method of broadening and stabilizing the effect of immunotherapy with a safe and effective synergistic approach, such as targeted photothermal immunotherapy, to achieve a long-lasting clinical outcome for an extended patient population.

SUMMARY

In some embodiments, the presently disclosed subject matter is directed to administering a therapeutically effective dose of nanoparticles and a therapeutically effective amount of an immune checkpoint modulator to a subject with a primary metastatic cancer and a distant metastatic site, wherein the nanoparticles concentrate at the primary cancer and at the distant metastatic site. The method further comprises inducing hyperthermia, ablation, or both at a site of the primary cancer with a photon radiation, wherein the plasmonics-active nanoparticles absorb the photon radiation and produce a localized photothermal therapy. The combination of the immune checkpoint modulator and the localized photothermal therapy results in damage to cells of the primary cancer and damage to cells at the distant metastatic site to treat the cancer.

In some embodiments, the presently disclosed subject matter is directed to a method of treating cancer comprising administering a therapeutically effective amount of plasmonics-active gold nanostars and a therapeutically effective amount of an anti-PD-L1 antibody to a subject with a primary metastatic cancer and a distant metastatic site, wherein the nanostar concentrates at the primary cancer and distant metastatic site. The method further comprises inducing hyperthermia, ablation, or both at a site of the primary cancer with a photon radiation, wherein the plasmonics-active nanoparticles absorb the photon radiation and produce a localized photothermal therapy. The combination of the anti-PD-L1 antibody and the localized photothermal therapy results in damage to cells of the primary cancer and damage to cells at the distant metastatic site to treat the cancer. The cancer can be selected from breast cancer, bladder cancer, color and rectal cancer, endometrial cancer, kidney cancer, leukemia, lung cancer, melanoma, mesothelioma, non-Hodgkin lymphoma, non-melanoma skin cancer, pancreatic cancer, prostate cancer, thyroid cancer, or combinations thereof.

In some embodiments, the presently disclosed subject matter is directed to a method of treating metastatic breast cancer. The method comprises administering a therapeutically effective dose of gold nanostars and a therapeutically effective amount of anti-PD-L1 antibody to a subject with a primary metastatic cancer and a distant metastatic site, wherein the nanoparticles concentrate at the primary cancer and at the distant metastatic site. The method further comprises inducing hyperthermia, ablation, or both at a site of the primary cancer with laser radiation, wherein the plasmonics-active nanoparticles absorb the laser radiation and produce a localized photothermal therapy. The combination of the anti-PD-L1 and the localized photothermal therapy results in damage to cells of the primary cancer and damage to cells at the distant metastatic site to treat the breast cancer.

In some embodiments, the presently disclosed subject matter is directed to a kit for treating cancer. Particularly, the kit comprises a therapeutically effective amount of a plasmonics-active metal nanoparticle for administration to a subject having a primary metastatic cancer for localization at the primary cancer and for absorption of a photon radiation and production of a localized photothermal therapy at a site of the primary cancer. The kit further comprises a therapeutically effective amount of an immune checkpoint modulator.

In some embodiments, the nanoparticles are plasmonics-active metal nanoparticles. In some embodiments, the metal nanoparticles comprise gold, silver, copper, aluminum, or metal oxide nanoparticles. In some embodiments, the nanoparticles comprise: a nanostar, a nanostar with a paramagnetic core, a void-space nanostar, a nanostar with an empty or dielectric core, a spherical or oval nanoparticle, a dielectric nanoparticle core covered with a metal nanocap, a spherical metal nanoshell covering a dielectric spheroid core, a multi-nanoparticle structure, a nanocube, a nanotriangle/nano-prism, a nanorod, a nanocylinder, a nanorasberry, a nanorattle, a nanocage, or combinations thereof. In some embodiments, the metal nanoparticles comprise gold nanostars having a plasmon peak of the nanostar ranging from about 600 nm to about 1000 nm. In some embodiments, the metal nanoparticles comprise a gold nanostars having a mean tip-to-tip diameter from 10-200 nm.

In some embodiments, the photon radiation is one or a combination of laser radiation, radio frequency radiation (RF), microwave radiation (MW), infrared radiation (IR), near infrared radiation (NIR), visible radiation (VIS), ultraviolet radiation (UV), X ray radiation, or photoacoustics radiation. In some embodiments, the administering of the nanoparticles is systemically by intravenous injection, by direct injection at the primary cancer site, by oral delivery, by adsorption, by deposition, or by combinations thereof. In some embodiments, the nanoparticles further comprise a bioreceptor to actively target the nanoparticles to cancer cells of the primary cancer and distant metastatic site. In some embodiments, the bioreceptor comprises an antibody, a DNA, a protein, a cell-surface receptor, a folate receptor, a peptide, or an aptamer.

In some embodiments, the immune checkpoint modulators target a costimulatory molecule selected from the group consisting of PD-1, PD-L1, CTLA-4, LAG3, B7-DC, ICOS, ICOSL, HVEM, LGIHT, CD40, CD40L, 4-1BB, 4-1BBL, OX40, OX40L, GITR, GITRL, TIM1, TIM3, TIM4, CD70, CD27, CD30, CD30L, BTLA4, and combinations thereof. In some embodiments, the immune checkpoint modulator comprises an anti-PD-L1 antibody.

DETAILED DESCRIPTION

Figure 1:
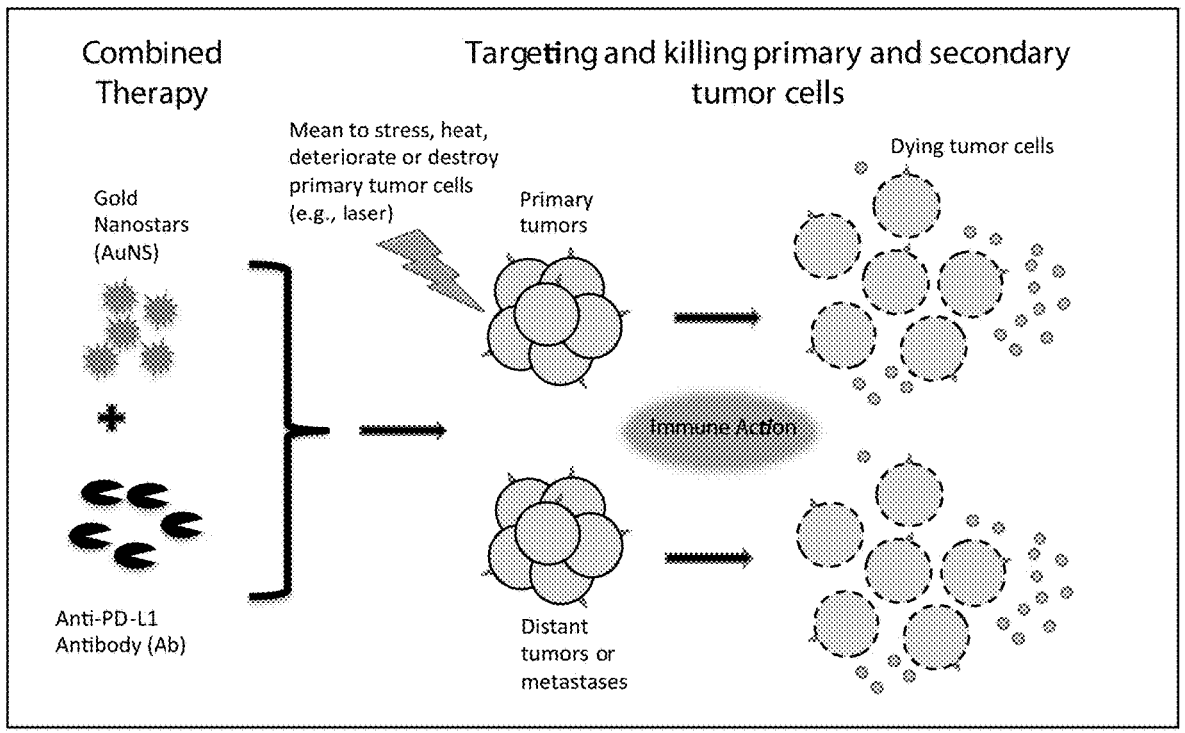
FIG. 1 is a schematic diagram representing a method of using two combined treatment modalities comprising a therapeutically effective amount of plasmonics-active metal nanoparticles (such as gold nanostars) and a therapeutically effective amount of an immune checkpoint modulator (such as PD-L1 antibody) to treat primary and secondary (distant) cancer cells in accordance with some embodiments of the presently disclosed subject matter.
Figure 2:
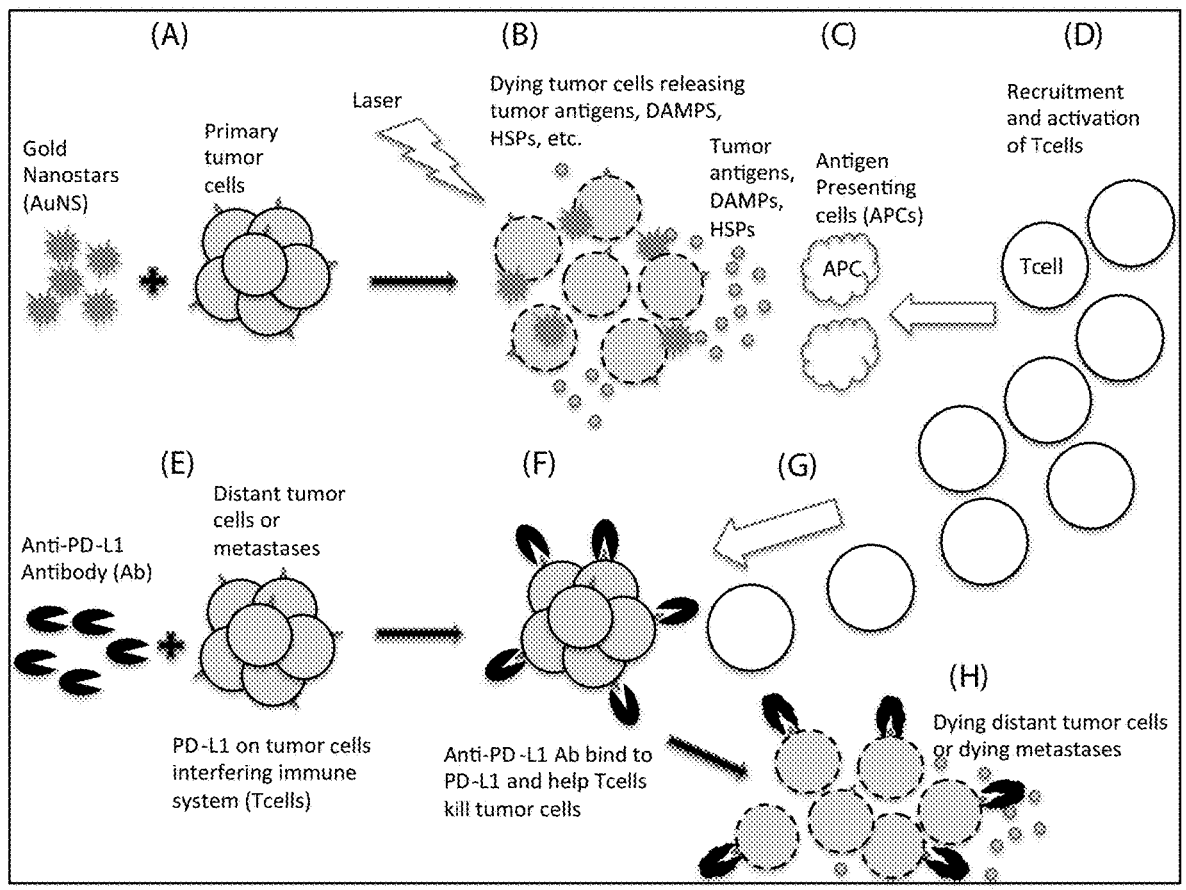
FIGS. 2A-2H are a schematic diagram of molecular mechanisms associated with the presently disclosed method in treating primary and secondary cancer cells in accordance with some embodiments of the presently disclosed subject matter.

All publications cited are hereby incorporated by reference. Unless defined otherwise, all technical and scientific terms used herein will have the commonly understood meaning to one of ordinary skill in the art to which the presently disclosed subject matter pertains.

It should be noted that as used herein and in the appended claims, the singular forms "a," "an," and "the" include plural reference unless the context clearly dictates otherwise. Thus, for example, a reference to "a population of entities" is a reference to one or more populations of entities and includes equivalents thereof known to those skilled in the art and so forth.

The term "about" as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 54 minutes to 66 minutes.

The term "cancer" as used herein refers to any disease of an organ or tissue characterized by poorly controlled or uncontrolled multiplication of normal or abnormal cells in that tissue that results in a tumor and has an effect on the body as a whole.

The terms "comprises" and "comprising" are intended to have the broad meaning ascribed to them in U.S. Patent Law and can mean "includes", "including" and the like.

The term "distant metastatic site" as used herein refers to a secondary tumor or area of abnormal cells growing at a site different from the site of the primary tumor.

As used herein, the term "hyperthermia" refers to heating up of a target higher than the environment equilibrium temperature.

As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health.

The term "photothermal therapy" as used herein refers to the use of compounds that generate heat upon exposure to light.

The term "primary tumor" as used herein refers to a tumor growing at the site of cancer origin.

The term "subject" used herein refers to an animal, such as a mammal. For example, mammals contemplated can include (but are not limited to) humans, primates, dogs, cats, sheep, cattle, goats, pigs, horses, mice, rats, rabbits, guinea pigs, and the like.

The phrase "therapeutically effective amount" as used herein refers to an amount that produces a desired effect at a reasonable benefit/risk ratio applicable to any medical treatment. In some embodiments, the effective amount can vary depending on such factors as the disease or condition being treated, the particular targeted constructs being administered, the size of the subject, and/or the severity of the disease or condition. One of ordinary skill in the art can empirically determine the effective amount of a particular compound without necessitating undue experimentation. In some embodiments, the therapeutically effective amount can alleviate at least one symptom of the disease or disorder.

The term "tumor" as used herein refers to abnormal mass of tissue that results from excessive cell division that is uncontrolled and progressive. Tumors can be either benign (not cancerous) or malignant.

The presently disclosed subject matter is directed to a method of treating cancer, such as (but not limited to) metastatic breast cancer and/or bladder cancer. As set forth in FIG. 1, the presently disclosed method comprises using two treatment modalities to synergistically treat primary and secondary cancer cells in a subject. The first element of the method comprises administering a therapeutically effective amount of nanoparticles (such as plasmonics-active metal nanoparticles) to a subject comprising a primary metastatic cancer and a distant metastatic site, wherein the nanoparticles concentrate at the primary cancer and at the distant metastatic site. The method further comprises exposing the subject to photon radiation at the site of the primary cancer. As a result, the plasmonics-active nanoparticle absorbs the photon radiation and induces hyperthermia, resulting in damage to the cells of the primary cancer. The second element of the disclosed method comprises administering a therapeutically effective amount of an immune checkpoint modulator to the subject. It is believed that the disruption of the tumor immunosuppressive environment synergistically combines with thermal damage to a large amount of cancer cells and with hyperthermia-enhanced innate and adaptive immune responses to treat the primary cancer as well as the distant cancer. The synergistic combination provides a rapid, safe, and effective treatment of local and distant lesions, better than each modality alone.

With regard to the first element of treatment, the subject is treated with a therapeutically effective amount of a nanoparticle, such as a plasmonics-active metal nanoparticle. The nanoparticles can be administered to the subject systemically, by intravenous injection, by direct injection at the primary tumor site, by oral delivery, by adsorption, by deposition, or by combinations thereof.

Various types of nanoparticles can be used with the disclosed method. For example, suitable nanoparticles can include (but are not limited to) plasmonics-active metal nanostars, nanostars with paramagnetic cores, a nanostar, a nanostar with a paramagnetic core, a void-space nanostar, a nanostar with an empty or dielectric core, a spherical or oval nanoparticle, a dielectric nanoparticle core covered with a metal nanocap, a spherical metal nanoshell covering a dielectric spheroid core, a multi-nanoparticle structure, a nanocube, a nanotriangle/nano-prism, a nanorod, a nanocylinder, nanorasberry, a nanorattle, a nanocage, or combinations thereof.

In some embodiments, the nanoparticle can be prepared using seed-mediated polymer-free synthesis methods that produce high yield monodisperse nanoparticles (such as gold nanostars).

Thus, in some embodiments, the nanoparticle can be a gold nanostar. The sharp points of the nanostar structure concentrate the local electromagnetic field, thereby enhancing the SERS signal and resulting, in some cases, zeptomolar detection sensitivity. Also, nanostars exhibit a strong two-photon action cross-section ($10^6$ Goeppert-Mayer units—a value higher than quantum dots or organic fluorophore), allowing the possibility of real-time particle imaging by two-photon absorption microscopy. The sharp branch points on nanostars can produce SERS "hot spots", due to the enhanced field around the sharp protrusion and/or as a result of coupled configurations (e.g., analyte molecule residing between two nanostars with sharp points of both nanostars interacting with the analyte). The sharp points and hot spots have been shown to powerfully enhance the electromagnetic field for improving photothermal therapy (PTT) and SERS detection.

Continuing, the nanoparticle can comprise any metal known or used in the art (i.e., gold, silver, copper, aluminum, metal oxide, and the like). For example, in some embodiments, the metal nanoparticle can be a gold or silver nanoparticle, which are considered to be biologically inert. In addition, gold nanostars are tunable in the NIR range, in the "therapeutic window" (700-1300 nm) where most biological components do not strongly absorb, thus allowing light penetration deeper in tissue for effective PTT and minimizing the interfering background often encountered in fluorescence for more sensitive SERS detection.

In some embodiments, the nanoparticle is surfactant-free to ensure there is no concern about the physiological effects of surfactant. In some embodiments, the nanoparticle can be non-toxic and constructed from a biocompatible material (such as gold). The size of nanoparticle used can be selected so that it can actively or passively concentrate in the tumor region due to an enhanced permeability and retention effect. In some embodiments, the nanoparticles have a mean tip-to-tip diameter of about 10-200 nm. Thus, the disclosed nanoparticles can have a mean tip-to-tip diameter of about 10-175 nm, 10-150 nm, 10-125 nm, or 10-100 nm in some embodiments.

The disclosed method includes the use of a device (such as a laser, MRI, etc.) to produce photon radiation. In some embodiments, the photon radiation can be laser radiation, radio frequency radiation (RF), microwave radiation (MW), infrared radiation (IR), near infrared radiation (NIR), visible radiation (VIS), ultraviolet radiation (UV), X ray radiation, and/or photoacoustics radiation. The nanoparticles function to convert light to heat with high efficiency to kill cancer cells. Alternatively or in addition, ultrasound can be used to produce thermal energy. The heat functions to stress, heat, deteriorate, and/or destroy the primary cancer cells.

Thus, in some embodiments, light having a wavelength within the therapeutic window (600-1300 nm) can be used to excite the metal nanoparticles. The nanoparticles exhibit plasmonics properties that selectively and strongly absorb laser excitation to produce efficient local photothermal therapy. The absorption band of the nanoparticles can be tuned to a desired wavelength (such as the therapeutic window). In some embodiments, the nanoparticle plasmon resonant wavelength and intensity correlate with the branch aspect ratio and length/number, so absorption bands can be tuned into near infrared (NIR) optical diagnostic/therapeutics window, where tissue absorption is minimal. The ability to selectively heat regions where nanoparticles are located while keeping surrounding tissues at significantly lower temperatures offers significant advantages compared to other methods of delivering thermal therapies. Rapid ablation can be achieved by nanostar-mediated photothermal therapy by exploting the natural propensity of nanoparticles to extravasate the tumor vascular network and accumulate in and around cancer cells. The enhanced permeability and retention (EPR) feature and the capacity to efficiently convert photon energy into heat, make metal nanoparticles (such as gold nanostars) suitable photothermal transducers for selective cancer therapy at the nanoscale level.

In some embodiments, the nanoparticles comprise a bioreceptor to actively target the nanoparticles to cancer cells of the primary tumor and distant metastatic site. For example, to specifically target disease cells, specific genes, and/or protein markers, the nanoparticles can be bound to a bioreptor (e.g., an antibody, DNA, protein, cell-surface receptor, folate receptors, peptides, aptamers, and other suitable ligands, etc.). The bioparticles can be immobilized to the nanoparticles using a wide variety of methods known and used in the art. For example, in some embodiments, binding can be performed through covalent bonds that take advantage of reactive groups (such as amine or sulfide) that naturally are present or can be incorporated into the biomolecule structure. In some embodiments, the binding can be achieved using N-hydroxysuccinimide and its derivatives, the use of maleimide, and/or the use of carboiimide, as would be known in the art.

The disclosed method also comprises administering a therapeutically effective amount of an immune checkpoint modulator to the subject. The immune checkpoint modulators disable immune checkpoints used by cancer cells to fend off the body's innate response. The immune checkpoint modulator can be administered to the subject systemically, by intravenous injection, by direct injection at the primary tumor site, by oral delivery, by adsorption, by deposition, or by combinations thereof. In some embodiments, immune checkpoint modulator functions to promote an immune response and/or to reverse immunosuppression. In some embodiments, the immune checkpoint modulator comprises a programmed death-ligand 1 (PD-L1) antibody, a cytotoxic T-lymphocyte-associated protein 4 (CTLA4) receptor, a B7-H3 molecule, an OX40/OX40L molecule, LAG3, B7-DC, ICOS, ICOSL, HVEM, LGIHT, CD40, CD40L, 4-1BB, 4-1BBL, OX40, OX40L, GITR, GITRL, TIM1, TIM3, TIM4, CD70, CD27, CD30, CD30L, BTLA4, and combinations thereof.

Programmed death-ligand 1 (PD-L1) is a transmembrane protein that contributes to the suppression of the immune system. Specifically, PD-L1 binds to the PD-1 receptor located on activated T cells, B cells, and myeloid cells to modulate T cell function. Tumor cells express antigens on the cell surface of major histocompatibility complex (MHC) molecules that the immune system can then recognize as danger or non-self. If an antigen is recognized and a permissive environment is present, the interaction of the T cell and the tumor cell can lead to a clonal expansion of T cells and the development of both activated cytotoxic CD8+ T cells as well as memory T cells. However, binding of PD-L1 to PD-1 receptor on the surface of T cells results in anergy or apoptosis of the T cells. The therapeutic anti-PD-L1 antibody is designed to block the PD-L1/PD-1 interaction and reverse tumor-mediated immunosuppression. The anti-PDL1 antibody targets PD-L1 expressed on cancer cells and cancer-infiltrating immune cells and prevents binding to PD-1 on the surface of T-cells. The anti-PD-L1 helps the activation of T cells as well as recruit other T cells to attack the cancer, thereby using the body's own immune system to fight multiple types of cancer.

CTLA4 is a protein receptor that, functioning as an immune checkpoint, downregulates immune responses. The levels of CTLA-4 expression in most resting T cells are extremely low (or absent), and CTLA-4 predominantly appears following T-cell activation. CTLA-4 is expressed by activated T cells and transmits a modulatory signal to T cells. Thus, CTLA4 plays a role in the inhibition of T cell activation. A CTLA4 receptor binds CTLA4, thereby preventing the transmission of a modulatory signal to T cells.

B7-H3 belongs to the B7 superfamily, a group of molecules that co-stimulate or down-modulate T-cell responses. B7-H3 serves as an accessory modulator of T-cell response. Specifically, B7-H3 stimulates T cell proliferation.

OX40 is a member of the tumor necrosis factor (TNF) receptor family and plays a key role in the survival and homeostasis of effector and memory T cells. An interaction between OX40 and OX40 ligand (OX40L) occurs when activated T cells bind to professional antigen-presenting cells (APCs). The T-cell functions, including cytokine production, expansion, and survival, are then enhanced by the OX40 costimulatory signals.

In addition, heat-stressed cells treated by nanoparticles release heat shock proteins that can further stimulate the immune system. Synergistic combination with immune checkpoint modulator treatment (such as anti-PD-L1 antibody) produces an immune response. For example, anti-PD-L1 antibody targets PD-L1 expressed on cancer cells and cancer-infiltrating immune cells, and prevents binding to PD-L1 on the surface of T cells.

The efficacy of the disclosed method is based on several synergistic processes. First, localized photothermal therapy using metal nanoparticles (such as gold nanostars) and photon radiation (such as NIR irradiation) can be used to kill primary cancer cells. After thermal ablation, dying cancer cells release tumor-specific antigens, damage-associated molecular pattern molecules (DAMPs), heat shock proteins (HSPs), etc. When cells are damaged or dying, DAMPS are released and acquire immunostimulatory properties. DAMPS have been shown to exert various effects on antigen-presenting cells (APCS), such as maturation, activation and antigen processing/presentation. APCs are present in the tissue or in local draining lymph nodes and function to process the tumor antigens and present tumor-derived peptides to T cells. Combining immune checkpoint modulator treatment with tumor antigen presentation activates tumor-specific T cells that attack both in the primary and distant metastatic cancer cells. The disclosed method synergistically enhances and broadens the effect of immune checkpoint modulators by combining both precise ablation of cancer cells and immunotherapy-boosting elevated temperature in the tumor microenvironment. Elevated fever-like temperatures have shown to extend and enhance the effects of various immunotherapies by activating and stimulating innate and adaptive immune responses. The immune system is triggered and heightened by several temperature-induced mechanisms, such as antigen presentation mediated by heat shock proteins (HSPs) and/or lymphocyte migration to lymphoid organs, the staging ground for immune defense. Immunotherapies can thus synergistically benefit from targeted thermal therapies, especially if hyperthermia (<43° C.) around immune-checkpoint modulators in the tumor bed is combined with precise thermal ablation of cancer cells.

FIGS. 2A-2H illustrate a schematic diagram of molecular mechanisms associated with the presently disclosed method in treating primary and secondary or metastatic (distant) cancer cells. It should be appreciated that other mechanisms can also be involved.

The ability to safely target single cancer cells with a high level of efficacy and specificity can be obtained using metal nanoparticles, such as gold nanostars that contain multiple sharp branches that act like "lightning rods" to safely and efficiently convert light into heat. The significant reduction of the laser energy needed to precisely destroy the targeted cancer cells in which the nanoparticles accumulate due to the enhanced permeation and retention (EPR) effect. The enhanced permeability and retention (EPR) effect is associated with the process by which particles or molecules of a certain size selectively accumulate in tumor tissue much more than they do in normal tissues. The EPR effect can be attributed to the fact that tumor cells grow quickly and need blood supply, a process called angiogenesis. The rapidly-formed new tumor vessels tend to be abnormal in form and architecture and leak more than normal vessels do. Also, there is a lack of effective lymphatic drainage in tumors. All of these factors lead to the EPR effect in tumors. Localized high temperature ablation within cancer cells also induces a mild temperature increase in tumor surroundings, where immune-blockade modulators operate. Thus the disruption of tumor immunosuppressive environment synergistically combines with thermal damage of a large amount of cancer cells and with hyperthermia-enhanced innate and adaptive immune responses.

Figure 3:
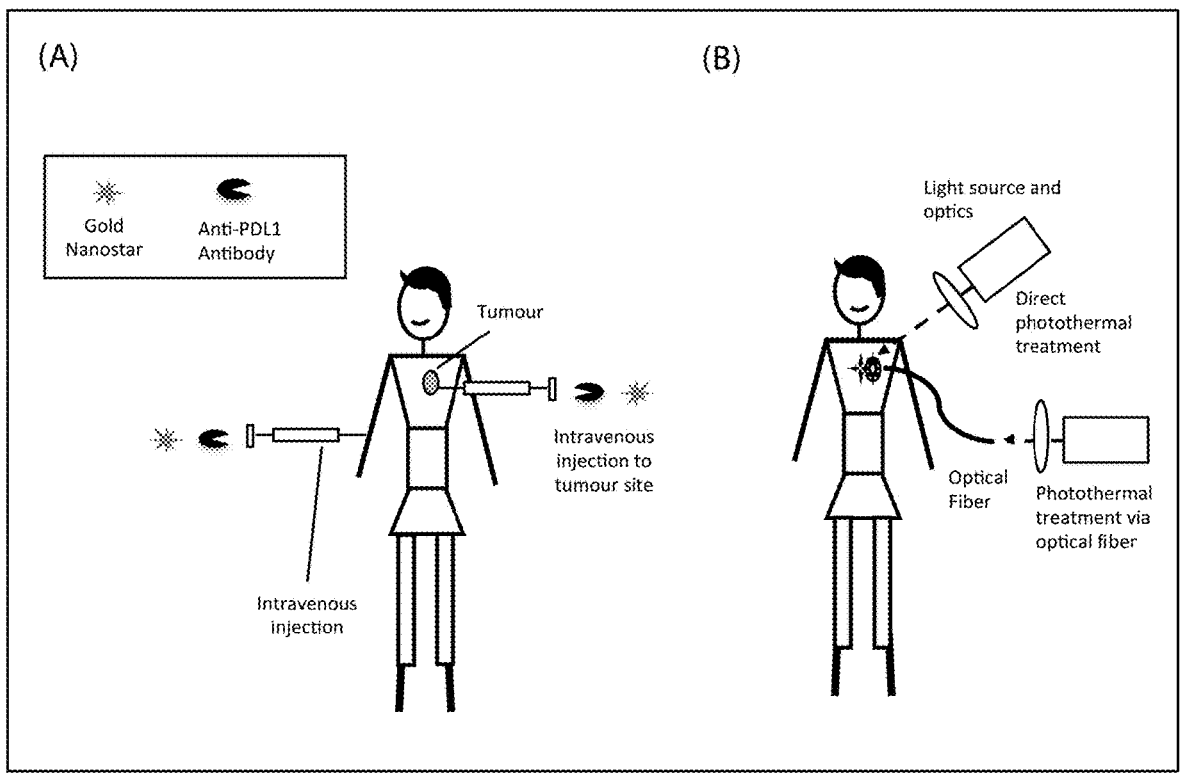
FIGS. 3A-3B illustrate the basic operating principle of the synergistic immuno photo nanotherapy modality in accordance with some embodiments of the presently disclosed subject matter.

The presently disclosed method (synergistic immune photothermal nanotherapy, "SYMPHONY") represents a significant breakthrough towards eradication of metastatic cancer deaths. The novel approach can provide an effective therapy when aggressive tumors cannot be surgically removed and eventually spread throughout the body. FIGS. 3A-3B illustrate the basic operating principle of the synergistic immuno photo nanotherapy modality. As shown, the metal nanoparticle (i.e., gold nanostars) and the immune checkpoint modulator (i.e., anti-PD-L1 antibodies) are administered to a subject systemically, by intravenous injection, orally, and/or by direct injection at the primary cancer site. The gold nanostars travel through the bloodstream inside the body towards the targeted tumor, either via passive or active targeting strategies known in the art. If the disease is systematic in nature, a photon radiation at suitable wavelengths (RF, MW, IR, NIR, VIS, UV, X ray) can be used to irradiate the tumor site, wherein the light is selected to penetrate deep inside tissue (e.g., NIR). In some embodiments, the photon radiation is one or a combination of laser radiation, radio frequency radiation (RF), microwave radiation (MW), infrared radiation (IR), near infrared radiation (NIR), visible radiation (VIS), ultraviolet radiation (UV), X ray radiation, or photoacoustics radiation. In some embodiments, tumors can also be treated with nanoparticles and/or radiation via catheters inserted into the tumor and/or via endoscopic or surgical access. For solid tumors, the radiation light source can be directed at the tumor. The heat can be used to kill diseased cells or tissues. If ablation is not possible (the tumor is positioned close to skin, for example), hyperthermia can be sufficient if properly fractionated over multiple weeks (e.g., one or more irradiations per week in some embodiments).

Localized photothermal therapy (PTT) using nanoparticles (such as gold nanostars) can be used to kill primary cancer cells. Upon treatment, dying cancer cells can release tumor antigens, DAMPS, HSPs, etc. In live cells, DAMPs are normally hidden, but are released and acquire immunostimulatory properties when the cell is injured or dying. DAMPS have been shown to exert various effects on antigen-presenting cells (APCs), such as maturation, activation and antigen processing/presentation. APCs, which are present in the tissue or in local draining lymph nodes, process the tumor antigens and present tumor-derived peptides to T cells. Combining immune checkpoint modulator (i.e., anti-PD-L1) treatment with tumor antigen presentation has the potential to activate tumor-specific T cells. The tumor cells, both in the primary site and at distant/metastatic site, can be recognized and attacked by host T cells.

The presently disclosed methods are particularly effective when the heat source comes from the inside of the tumor cells, since HSP thermal sensing can be triggered by cellular internal heating (not the surrounding environment). In particular, nanostars exhibit extremely high temperatures at their tips. If the tumor cells uptake even few nanostars, it will become thermally damaged well before the temperature of the surrounding medium reaches a thermal ablation dose (>55° C. for 1 minute).

In addition, the disclosed thermally enhanced immune checkpoint modulator immunotherapy can also be used with other electromagnetic energy sources. Particularly, photonics treatment modalities include both optical and non-optical technologies that deal with electromagnetic radiation, which is the energy propagated through space by electric and magnetic fields. The electromagnetic spectrum is the extent of that energy, ranging from gamma rays and X rays throughout ultraviolet, visible, infrared, microwave and radio frequency energy.

Successful treatment of advanced cancers could be potentially achieved by disabling immune checkpoints used by tumor cells to fend off the body's innate response. Immune checkpoint modulators have emerged as one of the most-promising modalities to treat systemic cancer, but they work only for a limited number of patients and can become ineffective with time. Broadening and stabilizing the effect of immune checkpoint modulators with nanoparticle-mediated synergistic thermal therapies could potentially address the overarching challenge of successfully treating cancer, such as metastatic breast cancer.

Treatment using metal nanoparticles and/or treatment using immune checkpoint modulators can be used in combination with one or more additional therapies. For example, the methods can be used in combination with vaccines or other immune stimulating therapies, such as dendritic cell vaccines and/or T-cell adoptive transfer. In some embodiments, the presently disclosed subject matter can be used in combination with radiotherapy. In some embodiments, the presently disclosed subject matter can be used in combination with treatments to deplete immunosuppressive cells and cytokines, such as tumor necrosis factor (TNF) and/or in combination with immune-stimulating cytokines (such as TGF, IL-1, IL-6, IL-10, IL-12, IL-18, etc.). In some embodiments, the presently disclosed subject matter can be used in combination with magnetic nanoparticles for magnetically inducing hyperthermia.

EXAMPLES

Example 1

Production of Gold Nanostars

Tetrachloroauric acid was reduced onto 12-nm citrate-stabilized gold seeds in an acidic environment using a weak reducing agent, ascorbic acid, and stabilized with sodium citrate. The synthesis was rapid, reproducible, and did not require a polymer as surfactant. Growth of the nanostars was completed in less than half a minute and the particles were stable at 4° C. for at least a week after centrifugal washing.

To obtain nanostars of different geometries while keeping the particle size in a similar range, multiple factors (including pH, vortexing speed, and concentration of $AgNO_3$, ascorbic acid, $HAuCl_4$ and seed) were investigated. It was observed that nanostars formed the most red-shift plasmon under lower pH, higher vortexing speed, and an ascorbic acid/$HAuCl_4$ ratio of 1.5~2. The concentration of $HAuCl_4$ and seeds were selected so the resulting nanostars sizes were around 60 nm. It was observed that silver ions played a role in controlling the formation of the star geometry. Without adding $Ag^+$ during synthesis, the resulting particles were polydisperse in both size and shape. The addition of a small amount of $Ag^+$ led to high-yield monodisperse star-shape particles. It was observed that the overall particles diameters synthesized under different $Ag^+$ concentrations were within 50~70 nm. Under higher $Ag^+$ concentration, sharper and more numerous branches were formed. The major role of $Ag^+$ was to assist the anisotropic growth of Au branches on multi-twinned citrate seeds, but not single crystalline CTAB seeds.

Example 2

Gold Nanostar Accumulation in Tumors and Local Photothermal Therapy Treatment (PTT)

Figures 4A, 4B:
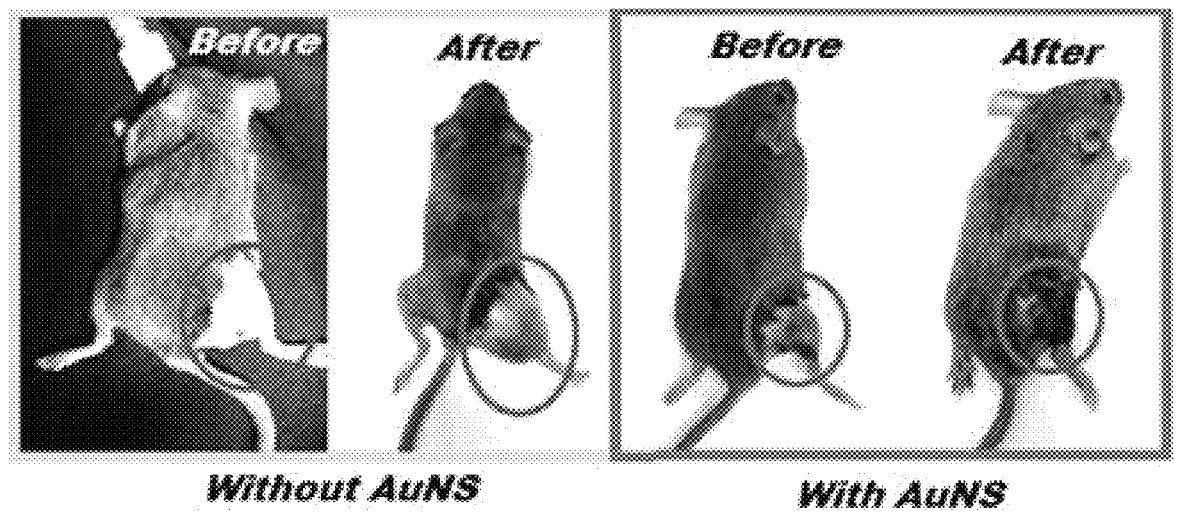
FIG. 4a shows images of mice having tumors before and after photothermal therapy without injection of gold nanostars.
FIG. 4b shows images of mice having tumors before and after photothermal therapy with gold nanostar injection.

Mice with a sarcoma on the right hind leg were obtained. The mice were injected with PEG-coated gold nanostars intravenously. FIGS. 4a and 4b show images of mice before (day 0) and after photothermal therapy (3 days after PTT), with and without injected gold nanostars. The images indicate a dramatic tumor size reduction attributed to PTT in the mouse injected with the gold nanostars, demonstrating the effectiveness of the EPR effect and the thermal PTT treatment.

Example 3

Demonstration of Synergistic Immuno Photo Nanotherapy

To demonstrate the synergistic immuno photo nanotherapy, preclinical experiments using a murine model were conducted. MB49 bladder cancer cells and 4T1 MBC cells were implanted into both flanks of C57BL/6 and white Balb/C mice respectively. After 14 days (~150 mm³ volume on right flank), animals were intravenously (IV) injected through the tail vein with gold nanostars at a dose of 2 mg in 100 µl of phosphate buffered saline (PBS) solution (Day 0). One day after nanostar injection (Day 1), the photothermal therapy treatment was performed with an 808-nm laser for 10 minutes at a low-power density of 0.6 W/cm² on the right flank tumor only. Within 1 hour of laser irradiation, anti-PD-L1 antibody (200 µg) was intraperitoneally injected and administration was repeated every 3 days until end of the study. For breast cancer mice, PTT was repeated on day 3. Tumor growth and body weight were monitored every 2 days. Humane endpoint euthanasia was performed if mice showed adverse reactions to treatments, lost greater than 15% of their body weight, or the tumor volume was greater than 1000 mm³. After 49 days for bladder cancer and 28 days for breast cancer, only PTT+Anti-PD-L1 group had survival mice 40% (2/5) in the bladder cancer study and 100% (8/8) in the MBC study, and all other groups (including anti-PD-L1 alone) had no survival.

Figure 5A:
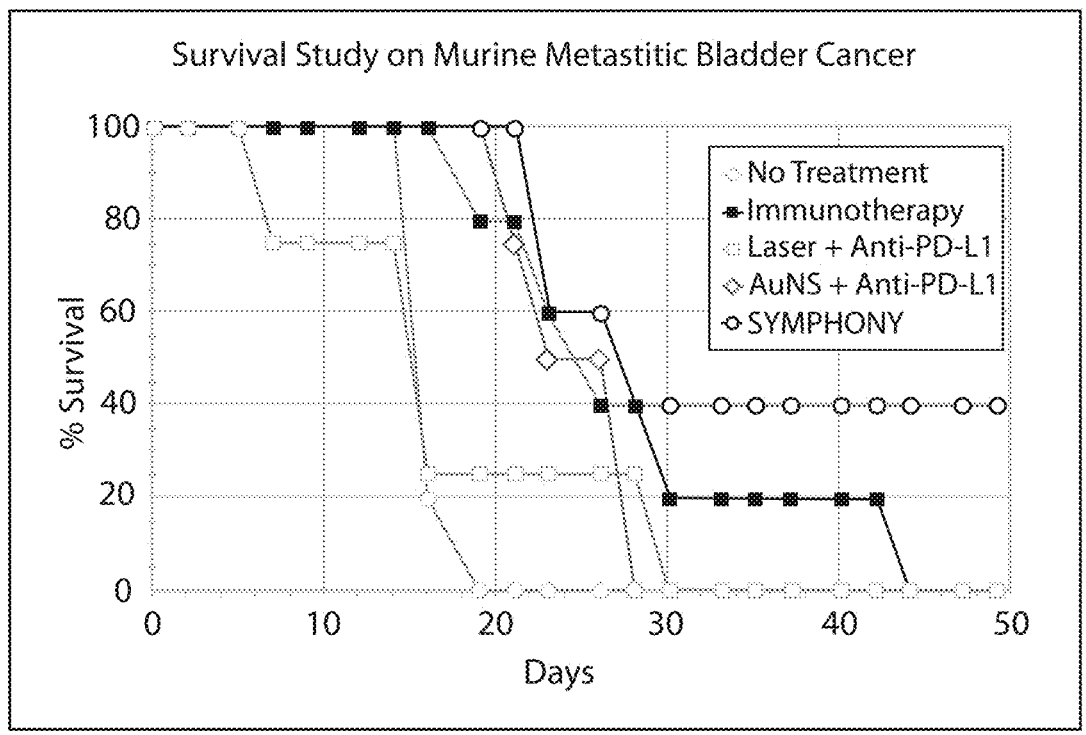
FIGS. 5a and 5b are Kaplan-Meier overall survival curves from a survival study of murine metastatic bladder cancer and metastatic triple-negative breast cancer, respectively.
Figure 5B:
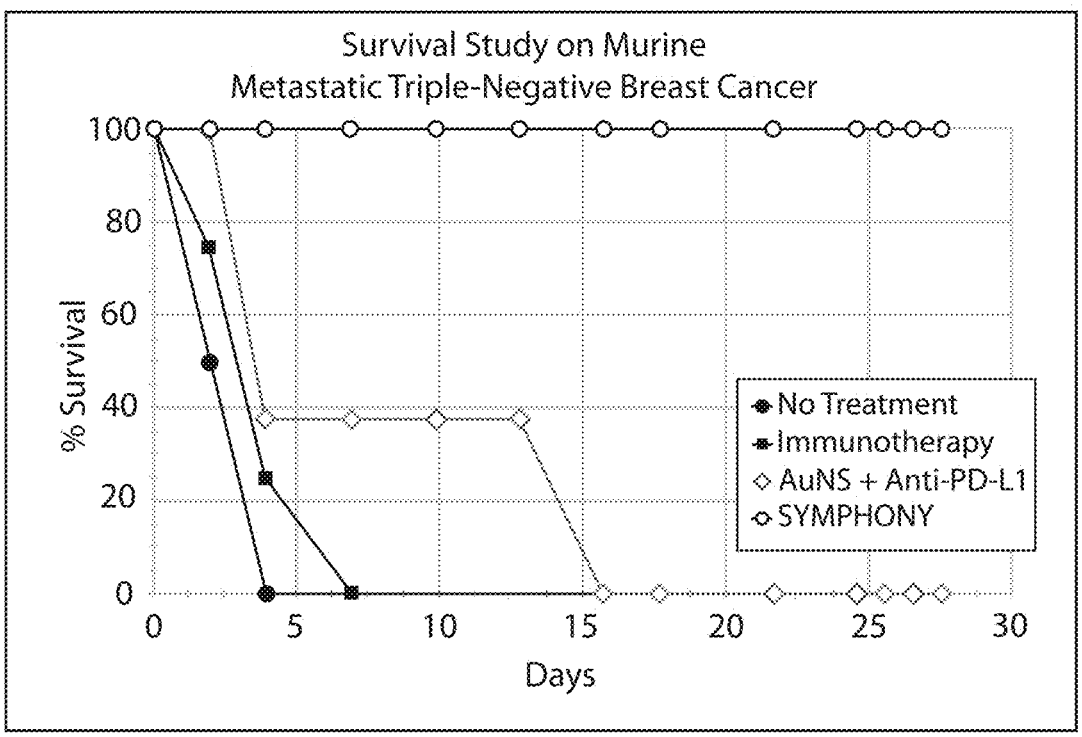

FIG. 5 illustrates a Kaplan-Meier overall survival curve showing significant benefit of combined gold nanostar-PTT and anti-PD-L1 therapy over anti-PD-L1 therapy alone. The overall survival curves of FIGS. 5a and 5b show significant benefit of combined AuNS-PTT+Anti-PD-L1 therapy over anti-PD-L1 therapy alone. Anti-PD-L1 treatment showed a survival benefit compared to the untreated control group, but was less effective than SYMPHONY therapy. It was noted that thermal fractionation may play a fundamental role since the dual PTT in MBC mice showed an improved survival rate compared to single PTT in bladder cancer mice. The studies show that the two-pronged approach can be effective in destroying untreated cancer sites distant from the primary tumor site at which photothermal therapy was applied.

Figure 6A:
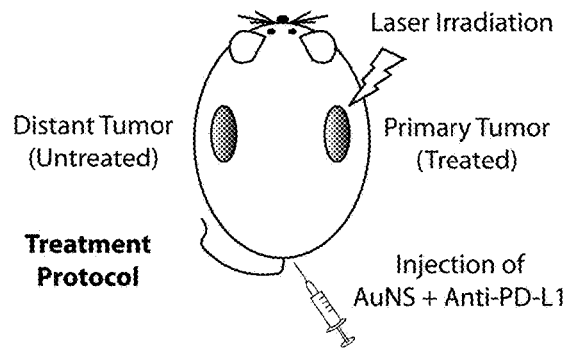
FIG. 6a is a representation of a two-pronged treatment modality in accordance with some embodiments of the presently disclosed subject matter.
Figure 6B:
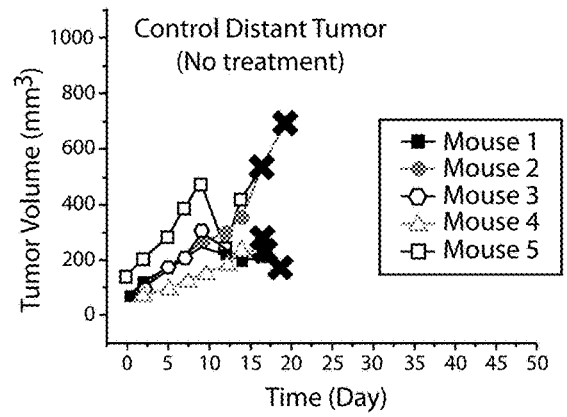
FIGS. 6b-6d are graphs of tumor volume versus time for control distant tumor without treatment, primary tumor with treatment, and distant tumor with treatment.
Figure 6C:
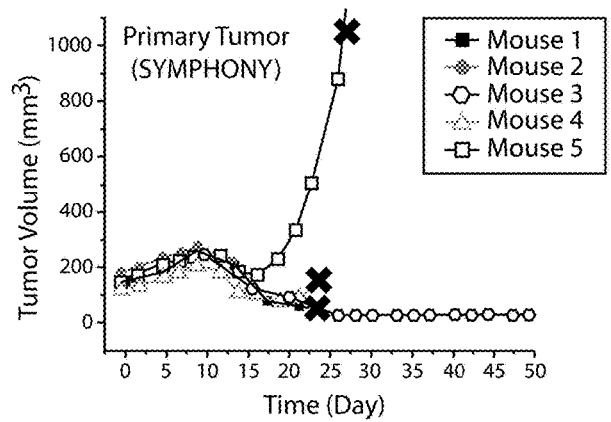
Figure 6D:
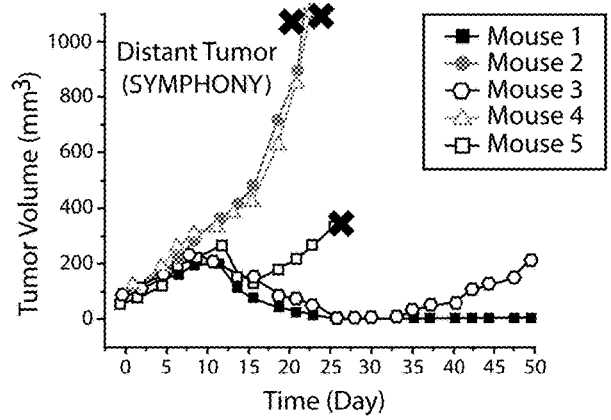

FIG. 6a illustrates the two-pronged SYMPHONY treatment modality, where the right flank tumor was treated with PTT and the left had no thermal exposure. FIG. 6b illustrates that the control tumor had strong cancer growth. As exemplified by the bladder cancer growth delay, the immediate killing effect at the primary tumor site (FIG. 6c) activated and enhanced the immune system (i.e., the untreated distant tumor also shrank, as shown in FIG. 6d).

The data shows a synergistic effect between AuNS-mediated photothermal treatment and anti-PD-L1 immune checkpoint modulator. The technology shows great promise to treat not only unresectable primary tumors, but also distant cancer metastasis by enhancing the systemic activity of specific and adaptive immune responses.

Example 4

Demonstration of Synergistic Immuno Photo Nanotherapy

Figure 7A:
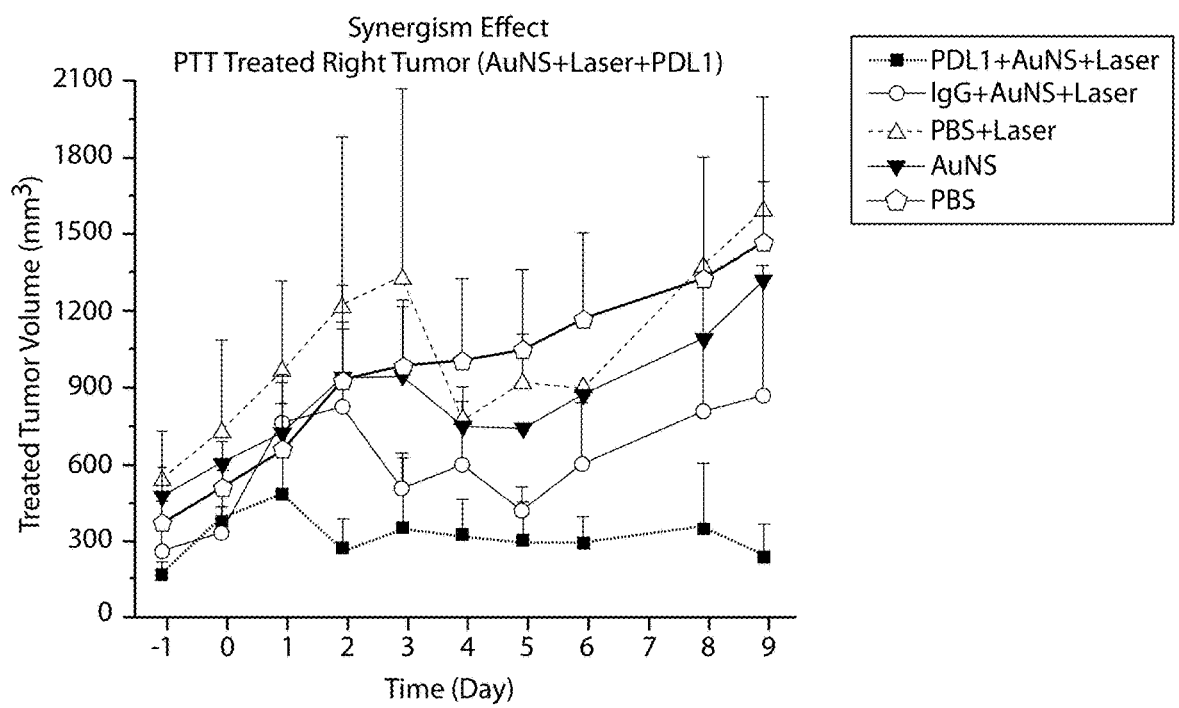
FIGS. 7a and 7b are graphs of treated tumor volume versus time and untreated (distant) tumor volume versus time, respectively.
Figure 7B:
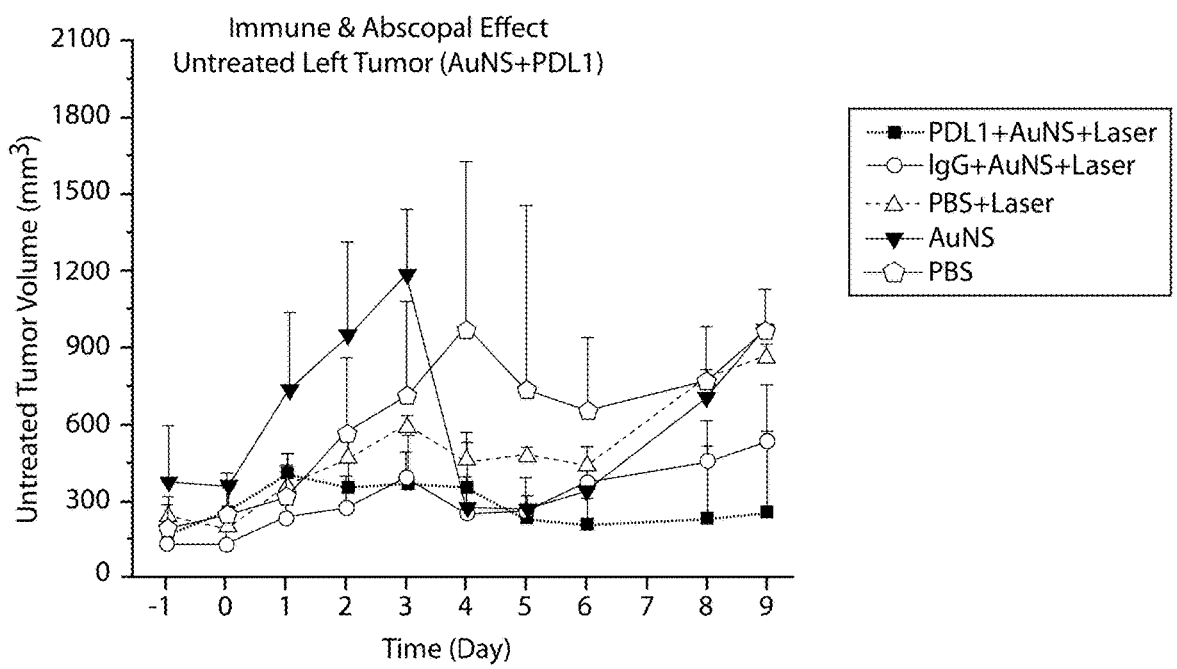

Gold nanostars were IV injected through the tail vein on day −1. Laser irradiation was performed on day 0 (10 minutes) and day 1 (5 minutes). The laser irradiation was only performed on the right flank tumor. Anti-PD-L1 antibody was IP injected on days 0, 3, 6, and 9. Each group contained 3-4 mice. The treated tumor volume was then measured over a 9-day period, as shown in FIGS. 7a and 7b. All mice in the three groups were sacrificed on day 9 due to large tumor sizes (total tumor volume >2000 mm³). Some mice had to be sacrificed as early as day 3 due to large tumor size.

The data shown in FIGS. 7a and 7b are the averaged tumor volume and the error bar is standard deviation. For clarity, the equivalent bottom bar for the standard deviation was not shown. It should be noted that the term "PD-L1 treatment" in the Figures designates anti-PD-L1 treatment.

The results for the treated mice in FIG. 7a indicate that photothermal therapy combined with anti-PD-L1 can stop tumor growth on the treated right tumor. In addition, anti-PDL1 treatment (PD-L1+AuNS+Laser curve) enhances photothermal therapy (IgG+AuNS+Laser curve).

The results for the treated mice in FIG. 7b indicate there is an immune abscopal effect observed on the left flank tumor that was not treated with photothermal therapy (NO laser irradiation) as the left tumor also stopped increasing in size. The data implies that the treatment of a primary tumor with nanostar hyperthermia and anti-PD-L1 treatment can result in disappearance of distant metastatic sites. PD-L1 treatment (PD-L1+AuNS+Laser curve) was shown to enhance photothermal therapy (IgG+AuNS+Laser).

Figure 8A:
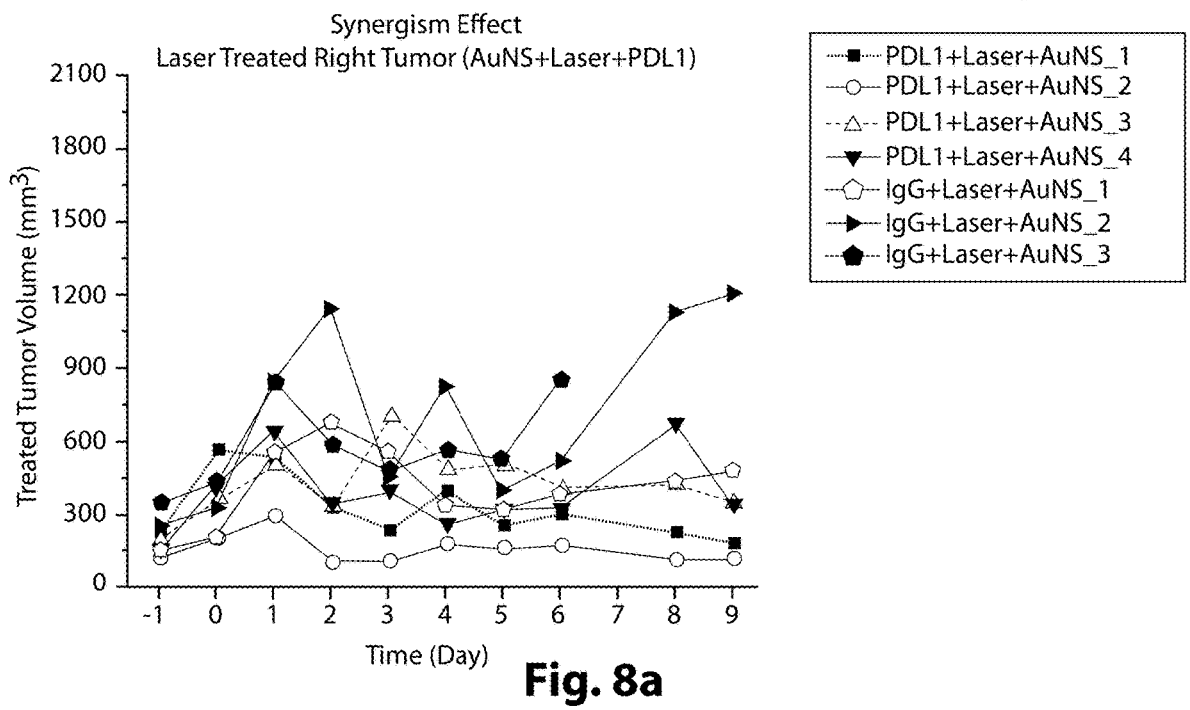
FIGS. 8a and 8b are graphs illustrating treated tumor volume versus time after treatment with gold nanostars+laser+PD-L1 and control, respectively.
Figure 8B:
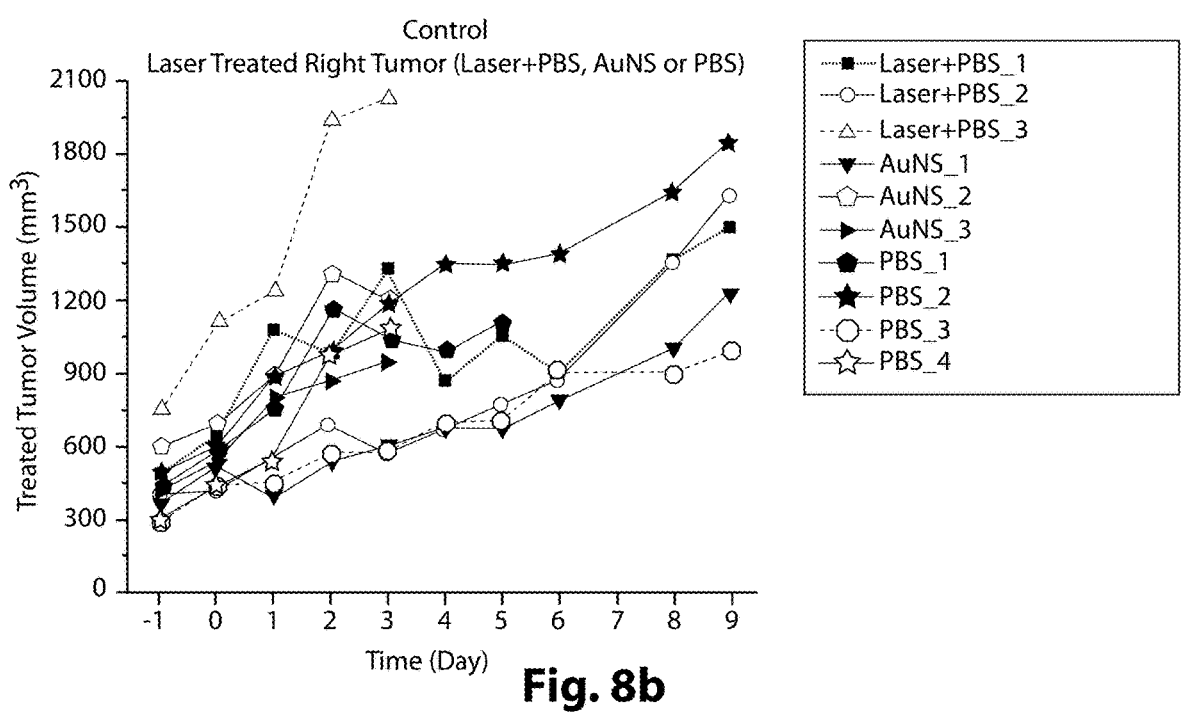

Detailed information on the treated tumor volume change is shown in FIGS. 8a and 8b. FIG. 8a illustrates that a combination of PD-L1, AuNS, and laser stops the laser-treated tumors from growing. It was noteworthy that for two mice (ID 1 and 2), mouse 1 had a decreased tumor volume 155 mm³ and mouse 2 had a decreased tumor volume of 108 mm³ on day 9, which was much smaller than the volume on day 0 (545 mm³ and 193 mm³, respectively). In addition, it is shown that anti-PD-L1 enhances the therapeutic effect from photothermal therapy. FIG. 8b illustrates that the tumor volumes of the control groups (Laser+PBS, AuNS, and PBS curves) kept growing. All mice in the 3 groups were sacrificed on day 9 due to their large tumor sizes (total tumor volume >2000 mm³). Some mice in the control group had to be sacrificed as early as day 3 due to large tumor size.

Figure 9A:
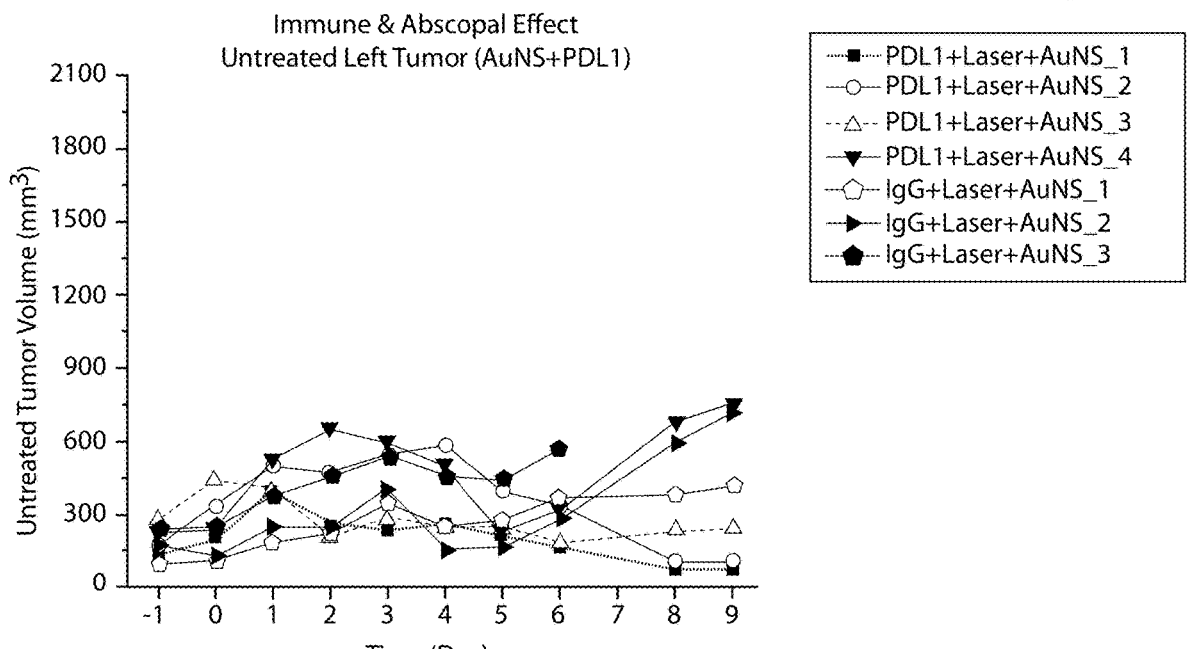
FIGS. 9a and 9b are graphs illustrating untreated tumor volume versus time after treatment with gold nanostars+PD-L1 and control, respectively.
Figure 9B:
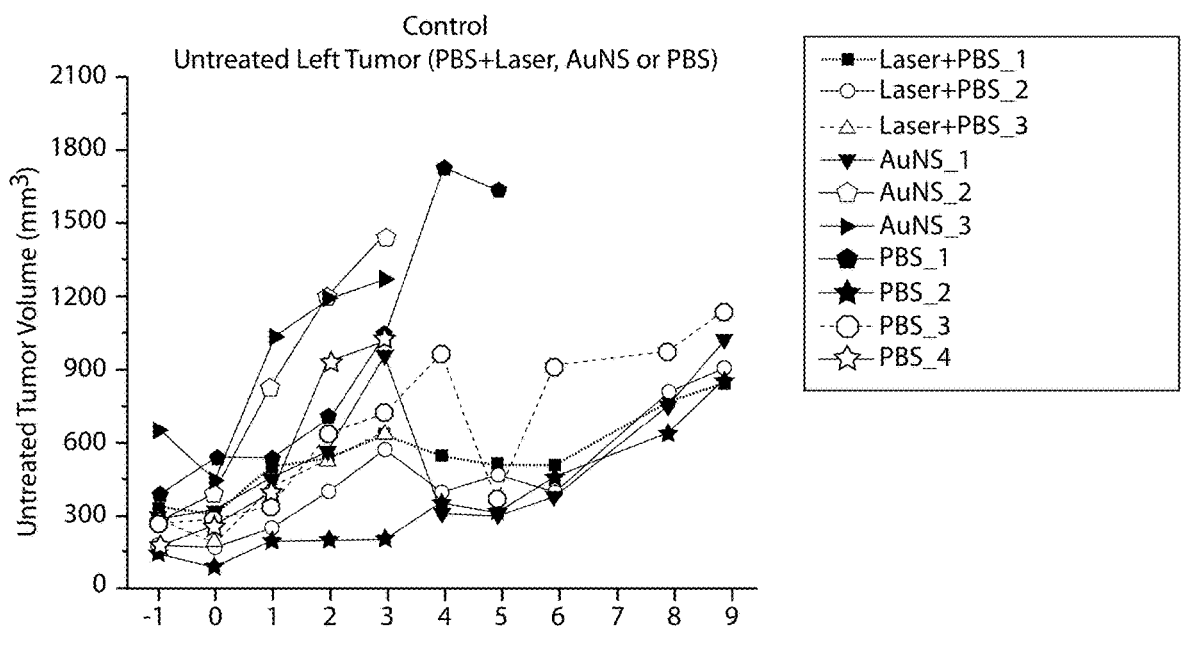

Detailed information on the untreated tumor volume change is set forth in FIGS. 9a and 9b. FIG. 9a illustrates that the combination of anti-PD-L1 and AuNS+laser stops growth of the laser-untreated tumor for 3 of 4 mice. For mouse ID 1, 2, and 3 in anti-PD-L1+AuNS+laser group, the laser untreated volume shrank from 203 mm³, 336 mm³, and 411 mm³ on day 0 to 79 mm³, 118 mm³, and 223 mm³ on day 9, respectively. The results shown in FIG. 9b indicate that the tumor volume in the Laser+PBS, AuNS, or PBS group kept growing and all mice in the 3 groups were sacrificed on day 9 due to large tumor volume (>2000 mm³). Some mice had to be sacrificed as early as day 3 due to large tumor size.

CONCLUSIONS

The experimental results show that the AuNS-Anti-PD-L1 system increased the photothermal therapy properties of the gold nanostars and the immunological properties of anti-PD-L1 antibodies alone. Nanophotothermal treatment using gold nanostars can be used to kill tumor cells. Importantly, the results show that gold nanostars can be selectively absorbed into tumor cells, due to the tumor's transport function and the EPR effect, which is an important process for local PTT treatment selective to tumor cells. The advantage of the gold nanostars and Anti-PD-L1 dual modality in its synergistic effect for tumor treatment is demonstrated in this study. Gold nanostars are designed to selectively absorb the 980 (or 810) nm laser light to heat up, ablate, and/or induce the killing of tumor cells, causing exogenous cellular stress, that could induce secretion of damage associated molecular pattern molecules (DAMPs). DAMPs and tumor antigens released by dying tumor cells can then be acquired at an increased rate by antigen-presenting cells (APCs) that are present in the tissue or in local draining lymph nodes. In a combined action, the anti-PD-L1 treatment, which targets immunosuppressive factors (PD-L1) present in the tumor cells, will promote increased activation of tumor-specific T cells in a synergistic manner. Hence, the AuNS-anti-PD-L1 acts as a perfect temporal-spatial continuum that connects cellular destruction and the immune response process, resulting in a synergistic photothermal immunological treatment. By treating one tumor on one side of the mice, the untreated tumor on the opposite side was clearly treated as well underlining the immunological abscopal effect. The effect involved the synergistic interaction between the selective photothermal reaction, immune-stimulation (production of DAMPs, HPS, recruitment of T-cells) and immunological targeting (i.e., blocking immunosuppressive factor PD-L1) at the tumor. The treatment acted as an integrated temporal-spatial continuum and the photothermal reaction by AuNS reduces the tumor burden and at the same time exposes the tumor antigens, DAMPs, HSPs, which together induced T-cell immune response.

The initial data demonstrates that the disclosed two-pronged therapeutic approach has been effective in inhibiting/destroying the primary cancer sites at which the therapy was applied as well as cancer sites distant from the tumor site at which the therapy was not applied. The results, show that the synergistic combination of immune triggering of PEN-PTT and immune de-suppression of anti-programmed death-ligand 1 (PD-L1) antibody generates an effective treatment of local and distant lesions, better than each modality alone.

REFERENCES

1. Ahmed, K., et al. (2015). "Hyperthermia: an effective strategy to induce apoptosis in cancer cells." Apoptosis 20(11): 1411-1419.
2. Albrecht, M. G., & Creighton, J. A. (1977). ? *J. Am. Chem. Soc.,* 99 (15), 5215-5217.
3. Boncheva, M., Scheibler, L., Lincoln, P., Vogel, H., & Akerman, B. (1999). *Langmuir,* 15, 4317-4320.
4. Burges, J. D., & Hawkridge, F. M. (1997). *Langmuir,* 13, 3781-3786.
5. Chao Wang, Ligeng Xu, Chao Liang, Jian Xiang, Rui Peng, Zhuang, Immunological Responses Triggered by Photothermal Therapy with Carbon Nanotubes in Combination with Anti-CTLA-4 Therapy to Inhibit Cancer Metastasis, Advanced Materials, Volume 26, Issue 48, 2014.
6. Chen, D. S., Irving, B. A., & Hodi, F. S. (2012). Molecular pathways: next-generation immunotherapy-inhibiting programmed death-ligand 1 and programmed death-1. *Clin Cancer Res.,* 18, 6580-6587.
7. Chen, D. S. and I. Mellman (2013). "Oncology Meets Immunology: The Cancer-Immunity Cycle." Immunity 39(1): 1-10.
8. Cheng. (2003). Synthesis of golf nanoparticles.
9. Chowdhury, F., et al. (2015). "PD-L1 and CD8(+)PD1(+) lymphocytes exist as targets in the pediatric tumor microenvironment for immunomodulatory therapy." Oncoimmunology 4(10): 8.
10. Eifler, A. C. and C. S. Thaxton (2011). Nanoparticle Therapeutics: FDA Approval, Clinical Trials, Regulatory Pathways, and Case Study. Biomedical Nanoetechnology: Methods and Protocols. S. J. Hurst. Totowa, Humana Press Inc. 726: 325-338.
11. S. S. Evans. E. A. Repasky, D. T. Fisher, Fever and the thermal regulation of immunity: the immune system feels the heat, Nature Reviews Immunology 15, 335-349 (2015).
12. Ewens A, Mihich E, Ehrke M J. Distant Metastasis from Subcutaneously Grown E0771 Medullary Breast Adenocarcinoma, Anticancer Research, 2005, vol. 25, no. 6B 3905-391.
13. Fales, A. M., Yuan, H., & Vo-Dinh, T. (2011). Silica-coated gold nanostars for combined surface-enhanced Raman scattering (SERS) detection and singlet-oxygen generation: a potential nanoplatform for theranostics. *Langmuir,* 27, 12186-90.
14. Fleischmann, Hendra, P. J., & McQuillan, A. J. (1974). ? *J. Chem. Phys. Lett.,* 26 (2), 163-166.
15. Gandra, N., H. C. Hendargo, S. J. Norton, A. M. Fales, G. M. Palmer, T Vo-Dinh, "Tunable and amplified Raman gold nanoprobes for effective tracking (TARGET): in vivo sensing and imaging", Nanoscale, 8 (16), 8486-8494 (2016).
16. Gandra, N., C. Portz, S. Z. Nergiz, A. Fales, T. Vo-Dinh and S. Singamaneni, "Inherently Stealth and Highly Tumor-Selective Gold Nanoraspberries for Photothermal Cancer Therapy". Nature Scientific Reports, 5:10311 (2015)
17. Garg, A. D., Nowis, D., Golab, J., Vandenabeele, P., Krysko, D. V., & Agostinis, P. (2010). Immunogenic cell death, DAMPs and anticancer therapeutics: an emerging amalgamation. *Biochim Biophys Acta,* 1805.
18. Gerben A. Koning, Alexander M. M. Eggermont, Lars H. Lindner, Timo L. M. ten Hagen, Hyperthermia and Thermosensitive Liposomes for Improved Delivery of Chemotherapeutic Drugs to Solid Tumors, Pharmaceutical Research 2010, Volume 27, Issue 8, pp 1750-1754.
19. Herne, T. M., & Tarlov, M. J. (1997). *J. Am. Chem. Soc.,* 119, 8916-8920.
20. Hirsch, L., Stafford, R. J., Bankson, J. A., Sershen, S. R., Rivera, B., Price, R. E., et al. (2003). Nanoshell-mediated near-infrared thermal therapy of tumors under magnetic resonance guidance. *PNAS,* 100 (23), 13549-13554.
21. Huang, X., Jain, P. K., El-Sayed, I. H., & El-Sayed, M. A. (2007). Plasmonic photothermal therapy (PPTT) using gold nanoparticles. *Lasers in Medical Science.*
22. Ito, A., Tanaka, K., Kondo, K., Shinkai, M., Honda, H., & Matsumoto, K. (2003). Tumor regression by combined immunotherapy and hyperthermia using magnetic nanoparticles in an experimental subcutaneous murine melanoma. *Cancer Science,* 94 (3), 308-313.
23. Jeanmaire, D. L., & Vanduyne, R. P. (1977). ? *J. Electroanal. Chem.,* 84 (1), 1-20.
24. Keir, M. E., Butte, M. J., Freeman, G. J., & Sharpe, A. H. (2008). PD-1 and its ligand in tolerance and immunity. *Annu Rev Immunol.,* 26, 677-704.
25. Khoury, C. and T. Vo-Dinh (2008). "Gold Nanostars For Surface-Enhanced Raman Scattering: Synthesis, Characterization and Optimization." J Phys Chem C 112(48): 18849-18859.

26. Liu, Y., et al. (2013). "Quintuple-modality (SERS-MRI-CT-TPL-PTT) plasmonic nanoprobe for theranostics." Nanoscale 5(24): 12126-12131.
27. Loo, C., et al. (2004). "Nanoshell-enabled photonics-based imaging and therapy of cancer." Technology in Cancer Research & Treatment 3(1): 33-40.
28. Maeda, H. (2001). "The enhanced permeability and retention (EPR) effect in tumor vasculature: the key role of tumor-selective macromolecular drug targeting." Adv Enzyme Regul 41: 189-207.
29. Ngo, H. T., N. Gandra, A. M. Fales, S. M. Taylor, T. Vo-Dinh, "Sensitive DNA detection and SNP discrimination using ultrabright SERS nanorattles and magnetic beads for malaria diagnostics", Biosensors and Bioelectronics, 81, 8-14 (2016).
30. Steel, A. B., Herne, T. M., & Tarlov, M. J. (1998). *Anal. Chem.*, 70, 4670-4677.
31. Takada T, Yamashita T, Sato M, Sato A, Ono I, Tamura Y, et al. Growth inhibition of re-challenge B16 melanoma transplant by conjugates of melanogenesis substrate and magnetite nanoparticles as the basis for developing melanoma-targeted chemo-thermo-immunotherapy. J Biomed Biotechnol 2009.
32. Tanaka K, Ito A, Kobayashi T, Kawamura T, Shimada S, Matsumoto K, Saida T, Honda H., Heat immunotherapy using magnetic nanoparticles and dendritic cells for T-lymphoma, J Biosci Bioeng. 2005 July; 100(1):112-5.
33. Tej K. Pandita, Shruti Pandita and Sukesh R. Bhaumik, Molecular Parameters of Hyperthermia for Radiosensitization, Crit Rev Eukaryot Gene Expr. 2009; 19(3): 235-251.
34. Toraya-Brown, S., Sheen, M. R., Zhang, P., Chen, L., Baird, J. R., Demidenko, E., et al. (2014). Potential Clinical Relevance of Local hyperthermia Treatment of Tumors Induces CD8+ T Cell-mediated Resistance against Distal and Secondary Tumors. *Nanomedicine: Nanotechnology, Biology and Medicine*, 10 (6), 1273-1285.
35. Tsan, M.-F., & Gao, B. (2009). Heat shock proteins and immune system. *Journal of Leukocyte Biology*, 85, 905.
36. Vo-Dinh, T. (1998). Surface-Enhanced Raman Spectroscopy Using Metallic Nanostructures. *Trends in Anal. Chem.*, 17, 557-582.
37. Vo-Dinh, T., et al. (2005). "Plasmonics-based nanostructures for surface-enhanced Raman scattering bioanalysis." Methods Mol Biol 300: 255-283.
38. Vo-Dinh, T., et al. (2013). "Plasmonic nanoprobes: from chemical sensing to medical diagnostics and therapy." Nanoscale 5(21): 10127-10140.
39. Vo-Dinh, t., & Seawaldt, V. (n.d.). Nanostars and Breast Cancer Targets.
40. Tuan Vo-Dinh, Brant Inman, Greg Palmer, Douglas Weitzel, Paolo Maccarini, Yang Liu, Synergistic Immuno Photo Nanotherapy Systems, Patent Application No. 62/182,734, Jun. 22, 2016.
41. Xia, X. H. and Y. N. Xia (2014). "Gold nanocages as multifunctional materials for nanomedicine." Frontiers of Physics 9(3): 378-384.
42. Yuan H, Fales A M, Vo-Dinh T. TAT peptide-functionalized gold nanostars: enhanced intracellular delivery and efficient NIR photothermal therapy using ultralow irradiance. Journal of the American Chemical Society. 2012 Jul. 18; 134(28):11358-61. PubMed PMID: 22734608.
43. Yuan H, Khoury C G, Hwang H, Wilson C M, Grant G A, Vo-Dinh T. Gold nanostars: surfactant-free synthesis, 3D modelling, and two-photon photoluminescence imaging. Nanotechnology. 2012 Feb. 24; 23(7):075102. PubMed PMID: 22260928. Pubmed Central PMCID: 3400343.
44. Yuan, H., et al. (2012). "In vivo particle tracking and photothermal ablation using plasmon-resonant gold nanostars." Nanomedicine 8(8): 1355-1363.
45. Yuan, H., et al. Nanomedicine: nanotechnology, biology, and medicine. 2012 November; 8(8):1355-63. PubMed PMID: 22370335. Pubmed Central PMCID: 3462891.

What is claimed is:

1. A method of treating primary tumors and metastatic cancer sites comprising:
   administering a therapeutically effective amount of plasmonics-active gold nanostars and a therapeutically effective amount of an anti-PD-L1 antibody to a subject with a primary tumor and a distant metastatic site, wherein the nanostar concentrates at the primary tumor and the distant metastatic site; and
   inducing hyperthermia, ablation, or both at a site of the primary tumor with laser radiation, wherein the plasmonics-active gold nanostars absorb the laser radiation and produce a localized photothermal therapy,
   wherein the combination of the anti-PD-L1 antibody and the localized photothermal therapy results in damage to cells of the primary tumor and damage to cells at the distant metastatic site to treat the cancer;
   wherein the cancer is selected from breast cancer and bladder cancer.

2. The method of claim 1, wherein the anti-PD-L1 antibody targets a costimulatory molecule selected from the group consisting of PD-1, PD-L1, CTLA-4, LAG3, B7-DC, ICOS, ICOSL, HVEM, LGIHT, CD40, CD40L, 4-1BB, 4-1BBL, OX40, OX40L, GITR, GITRL, TIM1, TIM3, TIM4, CD70, CD27, CD30, CD30L, BTLA4, TREM2, GM-CSF, and combinations thereof.

3. The method of claim 1, wherein the plasmonic-active gold nanostars have a plasmon peak ranging from about 600 nm to about 1000 nm.

4. The method of claim 3, wherein the plasmonics-active gold nanostars have a mean tip-to-tip diameter from 10-200 nm.

5. The method of claim 1, wherein the administering of the plasmonics-active gold nanostars is systemically by intravenous injection, by direct injection at the primary cancer site, by oral delivery, by adsorption, by deposition, or by combinations thereof.

* * * * *